(12) United States Patent
Reddy et al.

(10) Patent No.: US 7,485,609 B2
(45) Date of Patent: Feb. 3, 2009

(54) ENCAPSULATED LIQUID CLEANSER

(75) Inventors: Kiran K. Reddy, Roswell, GA (US); Ning Yang, Alpharetta, GA (US); John Richard Skerrett, Alpharetta, GA (US); Guy William Provenzano, Alpharetta, GA (US); Debra N. Welchel, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 518 days.

(21) Appl. No.: 11/238,341

(22) Filed: Sep. 29, 2005

(65) Prior Publication Data

US 2007/0072780 A1    Mar. 29, 2007

(51) Int. Cl.
*C11D 17/08* (2006.01)
*A61K 9/48* (2006.01)

(52) U.S. Cl. .................. 510/130; 510/120; 510/138; 510/141; 510/445; 424/451

(58) Field of Classification Search .............. 510/130, 510/120, 138, 141, 445; 424/451
See application file for complete search history.

(56) References Cited

U.S. PATENT DOCUMENTS

| | | | |
|---|---|---|---|
| 1,985,424 A | 12/1934 | Piggott | |
| 2,438,091 A | 3/1948 | Lynch | |
| 2,528,378 A | 10/1950 | Mannheimer | |
| 2,658,072 A | 11/1953 | Kosmin | |
| 2,703,798 A | 3/1955 | Schwartz | |
| 2,799,897 A | 7/1957 | Jansen | |
| 2,831,854 A | 4/1958 | Tucker et al. | |
| 2,965,576 A | 12/1960 | Wilson | |
| 3,245,972 A | 4/1966 | Anderson et al. | |
| 3,310,612 A | 3/1967 | Somerville, Jr. | |
| 3,389,194 A | 6/1968 | Somerville | |
| 3,423,489 A * | 1/1969 | Arens et al. | 264/4 |
| 3,516,941 A | 6/1970 | Matson | |
| 3,580,853 A | 5/1971 | Parran | |
| 3,617,588 A | 11/1971 | Langman | |
| 3,629,219 A | 12/1971 | Esker | |
| 3,779,942 A * | 12/1973 | Bolles | 428/402.2 |
| 3,855,191 A | 12/1974 | Doughty, Jr. et al. | |

(Continued)

FOREIGN PATENT DOCUMENTS

EP    0473270 B1    3/1995

(Continued)

OTHER PUBLICATIONS

Ziolkowsky B., "Neue Entwicklungstendenzen bei Umhuellungen von Produkten und Wirkstoffen," SÖFW—*Journal Seifen, Oele, Fette, Wachse, Verlag Fur Chemische Industrie*, Augsburg, DE, vol. 117, No. 5, Mar. 27, 1991, pp. 190-192.

(Continued)

*Primary Examiner*—Lorna M Douyon
(74) *Attorney, Agent, or Firm*—Nathan P. Hendon

(57) ABSTRACT

A personal cleansing article having a capsule and a liquid cleansing composition contained within the capsule is disclosed. The capsule is made to contain a trigger such that upon the occurrence of a specific event, the liquid cleansing composition is released from the capsule. A method for personal cleansing using such an article is also disclosed. Additionally, a method for manufacturing a foaming liquid cleansing composition is disclosed.

18 Claims, 3 Drawing Sheets

U.S. PATENT DOCUMENTS

| | | |
|---|---|---|
| 3,929,678 A | 12/1975 | Laughlin et al. |
| 3,936,573 A | 2/1976 | Brockett |
| 3,943,063 A | 3/1976 | Morishita et al. |
| RE28,779 E | 4/1976 | Katayama et al. |
| 3,956,172 A | 5/1976 | Saeki et al. |
| 3,963,699 A | 6/1976 | Rizzi et al. |
| 3,971,852 A | 7/1976 | Brenner et al. |
| 4,001,211 A | 1/1977 | Sarkar |
| 4,005,195 A | 1/1977 | Jandacek |
| 4,005,196 A | 1/1977 | Jandacek et al. |
| 4,016,098 A | 4/1977 | Saeki et al. |
| 4,066,568 A | 1/1978 | Nakazawa et al. |
| 4,115,315 A | 9/1978 | Marinelli |
| 4,124,521 A | 11/1978 | Jedzinak |
| 4,138,013 A | 2/1979 | Okajima |
| 4,189,551 A | 2/1980 | Gangal |
| 4,197,346 A | 4/1980 | Stevens |
| 4,211,437 A | 7/1980 | Myers et al. |
| 4,218,506 A | 8/1980 | Oda et al. |
| 4,263,251 A | 4/1981 | Voegle |
| 4,265,926 A | 5/1981 | Sperti et al. |
| 4,278,633 A | 7/1981 | Fujii |
| 4,294,921 A | 10/1981 | Yamaguchi et al. |
| 4,305,502 A | 12/1981 | Gregory et al. |
| 4,349,470 A | 9/1982 | Battista |
| 4,386,106 A | 5/1983 | Merritt et al. |
| 4,394,287 A | 7/1983 | Scarpelli |
| 4,442,194 A | 4/1984 | Mikami |
| 4,450,877 A | 5/1984 | Walker et al. |
| 4,517,360 A | 5/1985 | Volpenhein |
| 4,518,772 A | 5/1985 | Volpenhein |
| 4,557,853 A | 12/1985 | Collins |
| 4,586,060 A | 4/1986 | Vassiliades |
| 4,777,089 A | 10/1988 | Takizawa et al. |
| 4,780,316 A | 10/1988 | Brox |
| 4,797,300 A | 1/1989 | Jandacek et al. |
| 4,898,781 A | 2/1990 | Onouchi et al. |
| 4,908,233 A | 3/1990 | Takizawa et al. |
| 4,937,370 A | 6/1990 | Sabatelli |
| 4,976,953 A | 12/1990 | Orr et al. |
| 4,978,483 A | 12/1990 | Redding, Jr. |
| 4,985,459 A | 1/1991 | Sunshine et al. |
| 4,999,186 A | 3/1991 | Sabatelli et al. |
| 5,063,057 A | 11/1991 | Spellman et al. |
| 5,064,650 A | 11/1991 | Lew |
| 5,069,897 A | 12/1991 | Orr |
| 5,073,371 A | 12/1991 | Turner et al. |
| 5,073,372 A | 12/1991 | Turner et al. |
| 5,087,445 A | 2/1992 | Haffey et al. |
| 5,180,637 A | 1/1993 | Sumii |
| 5,306,515 A | 4/1994 | Letton et al. |
| 5,306,516 A | 4/1994 | Letton et al. |
| 5,330,835 A | 7/1994 | Kikuchi et al. |
| 5,364,617 A | 11/1994 | Bush et al. |
| 5,385,737 A | 1/1995 | Shigeno et al. |
| 5,416,196 A | 5/1995 | Kitabatake et al. |
| 5,441,660 A | 8/1995 | Tsaur et al. |
| 5,462,963 A | 10/1995 | Bush et al. |
| 5,487,884 A | 1/1996 | Bissett et al. |
| 5,686,082 A | 11/1997 | N'Guyen |
| 5,686,367 A | 11/1997 | Hayashi |
| 5,837,274 A | 11/1998 | Shick et al. |
| 5,846,927 A | 12/1998 | Vasudevan |
| 5,910,455 A | 6/1999 | Maddern et al. |
| 6,068,834 A | 5/2000 | Kvalnes et al. |
| 6,093,411 A | 7/2000 | Bissett |
| 6,103,269 A | 8/2000 | Wunderlich et al. |
| 6,103,378 A | 8/2000 | Yao et al. |
| 6,238,616 B1 | 5/2001 | Ishikawa et al. |
| 6,238,626 B1 | 5/2001 | Higuchi et al. |
| 6,238,678 B1 | 5/2001 | Oblong |
| 6,279,656 B1 | 8/2001 | Sinclair et al. |
| 6,294,186 B1 | 9/2001 | Beerse et al. |
| 6,333,047 B1 | 12/2001 | Katagihara et al. |
| 6,362,146 B1 | 3/2002 | Macaulay |
| 6,420,333 B1 | 7/2002 | Hsu et al. |
| 6,432,429 B1 | 8/2002 | Maddern et al. |
| 6,592,844 B2 | 7/2003 | Coombes et al. |
| 6,752,953 B2 | 6/2004 | Chen et al. |
| 6,806,213 B2 | 10/2004 | Brooks |
| 6,833,340 B2 * | 12/2004 | Lefenfeld et al. ............ 510/191 |
| 6,849,584 B2 * | 2/2005 | Geary et al. ................ 510/119 |
| 2002/0034486 A1 * | 3/2002 | Midha et al. ................ 424/70.2 |
| 2002/0061954 A1 | 5/2002 | Davis et al. |
| 2003/0086973 A1 | 5/2003 | Sowden et al. |
| 2003/0199404 A1 * | 10/2003 | Lorenzi et al. ............... 510/119 |
| 2004/0115378 A1 | 6/2004 | Dunaway et al. |
| 2004/0169299 A1 | 9/2004 | Davis et al. |
| 2005/0067726 A1 | 3/2005 | Yan et al. |
| 2005/0153862 A1 | 7/2005 | Lau et al. |
| 2005/0279755 A1 * | 12/2005 | Jansen .......................... 221/9 |

FOREIGN PATENT DOCUMENTS

| | | | |
|---|---|---|---|
| EP | 1421872 A2 | | 5/2004 |
| EP | 1430947 A1 | | 6/2004 |
| EP | 1577375 A2 | | 9/2005 |
| GB | 1307387 | * | 2/1973 |
| WO | WO 01/34829 | | 5/2001 |
| WO | WO 2004/041991 | | 5/2004 |

OTHER PUBLICATIONS

Kinekawa, Y. et al., "Turbidity and Rheological Properties of Gels and Sols Prepared by Heating Process Whey Protein," *Bioscience, Biotechnology, and Biochemistry*, vol. 59, No. 5, May 1995, pp. 834-840.

Kitabatake, N. et al., "Viscous Sol and Gel Formation from Process Whey Protein Below 25° C.," *Journal of Food Science*, vol. 61, No. 3, May-Jun. 1996, pp. 500-503.

Molyneaux, P., *Water-Soluble Synthetic Polymers: Properties and Behavior*, vol. 1, ISBN 0-8493-6135-4, 1983, pp. 84-92.

Schulz, R.C., "Acrylamide Polymers," *Encyclopedia of Polymer Science and Engineering*, vol. 1, John Wiley & Sons, Inc., NY, 1985, pp. 169-211.

McCutcheon's, Emulsifiers & Detergents, North American Edition, 1986, pp. 317-319.

\* cited by examiner

ENCAPSULATED LIQUID CLEANSER

BACKGROUND

The health and hygiene benefits associated with regular and frequent hand washing have been understood throughout human history. Soap has been around for nearly as long as the benefits of washing have been understood. Through the years soap has evolved through many formulations and forms to meet the needs of the cleansing public.

Soap has been available in a bar form for most of its known existence. While a convenient form when placed near a water source in one's own dwelling, a bar of soap is not always convenient or sanitary outside the home. First, a bar of soap is not a very convenient form for a person to transport from place to place, especially when the bar is wet. Secondly, in a public setting, a bar of soap that is available for one and all to use can be unsanitary and uninviting for personal use.

One early solution dealing with the issue of soap sharing was the use of powdered soap dispensers in public restrooms and at communal washbasins within factories. Such dispensers allowed individuals to dispense appropriate amounts of the powdered soap to themselves. However, such soap was messy and left deposits of soap within washbasins. Additionally, the powdered soap needed to be contained and did not lend itself to easy transport if a person wished to take soap elsewhere.

Liquid soap is another soap form that solves the issue with sanitary individual soap use; the user need only dispense the amount of liquid soap that they wish to use themselves. However, such soap requires a dispenser in which to contain and to dispense the soap. Additionally, such soap is more expensive to distribute as a majority of the soap's weight is contributed by the water that makes up a large proportion of the liquid soap formulation.

More recently, soap has been available in a gel or a liquid/solid combination that eliminates much of the water that is used in liquid soaps. Such soaps ship as a solid, but have formulations that quickly lather with water. The gel soaps again allow for individual dispensing of soap, but they also require dispensers to contain and dispense the gel soap.

SUMMARY OF THE INVENTION

In light of the problems and issues discussed above, it is desired to have a cleansing composition that an individual could have available in a discrete amount for use wherever the individual finds convenient or necessary. It is further desired that the cleansing composition be available in a form that is easily and convenient to transport.

The present invention is directed to a personal cleansing article made of a capsule and a liquid cleansing composition contained within the capsule. The capsule has a trigger such that upon occurrence of a specific event, the capsule releases the liquid cleansing composition to the consumer. The trigger may be a capsule with a water-soluble shell that releases the composition when the capsule is exposed to water. Alternatively, the trigger may be a pressure-sensitive shell that releases the composition when the capsule is exposed to an external pressure source. In other embodiments the trigger may be a combination of a water-soluble and a pressure sensitive shell.

In various embodiments of the invention, the shell may be an interlocking outer shell assembly having a first outer shell and a second outer shell adapted to interlock or may be a seamless shell. In some embodiments that capsule may also have a barrier layer on the interior surface of the shell. Such a barrier layer may be a layer of microcrystalline wax in some embodiments. In other embodiments, the capsule may contain a plurality of micro-capsules, where the liquid cleansing composition is encapsulated within such micro-capsules.

The liquid cleansing composition may be an aqueous based composition having one or more surfactants. In some embodiments the composition is adapted such that at least one of the surfactants within the liquid cleansing formulation will form an interfacial barrier between the inside surface of the capsule and the liquid cleansing formulation. In alternate embodiments, the composition may also have a co-surfactant or a therapeutic benefit agent.

In some embodiments, the liquid cleansing composition may have a foaming agent. Such a foaming agent may be a propellant gas. In further embodiments of compositions having a foaming agent, the composition may have a fluorinated surfactant.

The present invention is also directed to a method for personal cleansing comprising the steps of providing a single-dose capsule containing a liquid cleansing composition; triggering the capsule to release the liquid cleansing composition from the capsule; and cleansing with the liquid cleansing composition. Such triggering may include exposing the capsule to water, exposing the capsule to an external pressure source, or exposure to a combination of water and pressure.

In some embodiments the method may also include the step of foaming the liquid cleansing composition after triggering the release of the composition and prior to cleansing with the composition. In other embodiments the method may include providing more than one single-dose capsules containing liquid cleansing composition and triggering all of the capsules to release the liquid cleaning composition prior to cleansing with the composition.

Finally, the present invention is also directed to a method for manufacturing a foaming liquid cleansing composition capsule. The method includes the steps of providing a capsule shell material; forming a capsule from the capsule shell material; providing a pressurized enclosure; conveying the capsule into the pressurized enclosure; filling the capsule with a mixture of a liquid cleansing composition and a propellant gas; injecting a propellant gas into the liquid cleansing composition within the capsule; closing and sealing the capsule; and conveying the finished capsule from the pressurized enclosure.

DETAILED DESCRIPTION

The present invention relates to capsules that contain a liquid cleansing composition that may be released to the user upon triggering of the capsule shell material. As used herein, the terms "trigger", "triggering", and "triggered" refer to the initiation of the release of the liquid cleansing composition from the capsule by a specific event. Such capsules provide a single-dose of a liquid cleansing composition of sufficient volume to meet the personal cleansing needs of a consumer.

In some embodiments, multiple smaller capsules may be used to deliver the sufficient volume of liquid cleansing composition to meet consumer cleansing needs.

By encapsulating the liquid cleansing composition within a capsule, not only can the consumer obtain a single-dose of such a composition, but the composition itself is fully contained, thus reducing the concern of leakage that is common with liquid soap dispensers, as discussed above. Additionally, the liquid cleansing composition encapsulated within the capsules may also be a concentrated cleansing composition that works with water to provide the finished cleansing composition in use. This functionality would minimize the issue of transporting mostly water weight as occurs with liquid soaps, as discussed above.

Figure 1:
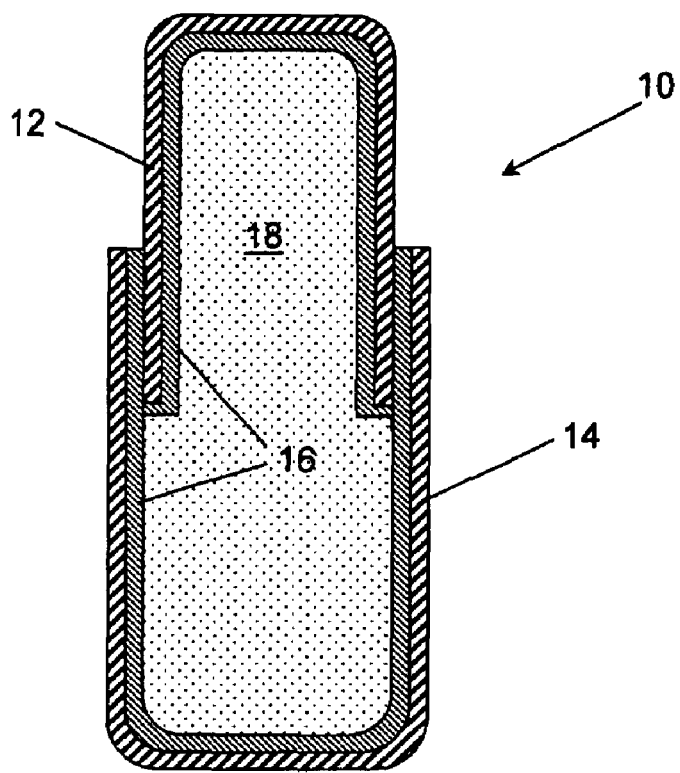
FIG. 1 is a cross sectional view of an interlocking shell capsule embodiment of the present invention.
Figure 2:
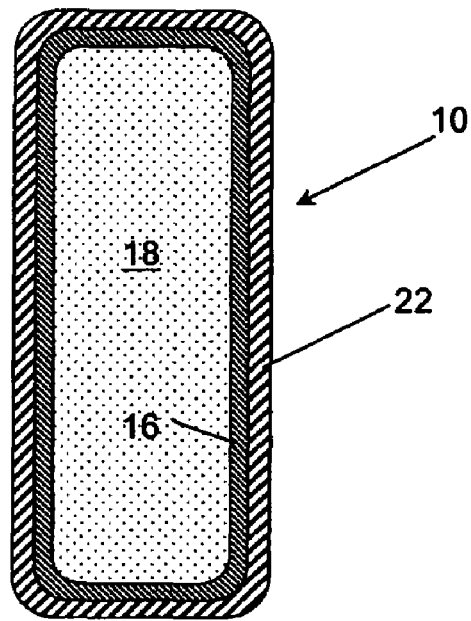
FIG. 2 is a cross sectional view of a seamless shell capsule embodiment of the present invention.

Examples of the capsules 10 of the present invention are illustrated in FIGS. 1 and 2. As illustrated in both figures, the capsules are shown as "capsule-shaped", i.e., the shape is similar to the shape of capsules that are commonly found for uses such as medicine, nutritional supplements and the like. More particularly, the capsules 10 are generally cylindrical with rounded ends. Such a shape is commonly understood and equipment for producing such capsules is readily available. The capsules 10 are generally in the size range of approximately 6 mm to 26 mm in diameter and 13 mm to 90 mm in length. However, it is clear to those skilled in the art that modification of such a shape and size, or the use of capsules of different shapes and sizes, may be possible.

FIG. 1 shows an embodiment of the capsule 10 of the present invention made of two interlocking outer shell components. The first outer shell 12 fits snuggly within the second outer shell 14 and engages the second outer shell 14 in such a way that the first outer shell 12 does not easily release from the second outer shell 14. The liquid cleansing composition 18 is encapsulated inside of the shell components 12, 14. Alternatively, FIG. 2 shows another embodiment of the capsule 10 of the present invention made as a seamless outer shell 22. Such a shell is made by a different process, but also encapsulates the liquid cleansing composition 18 within the capsule 10.

In use, the capsules are delivered to the consumer as one or more capsules 10 containing the liquid cleansing composition 18. Upon the occurrence of a specific triggering event, the liquid cleansing composition 18 is released from the capsule 10 for use by the consumer. The triggering event that releases the composition 18 is dependent on the specific trigger built into the capsule 10 design. It is desired that the capsules 10 will be triggered by exposure to water, by external pressure, or by a combination of both water and pressure.

For example, the capsule 10 of FIG. 2 may be made of an outer shell material 22 that is water soluble. When such a capsule 10 is exposed to water (e.g., in the hands of a consumer held under a water source) the outer shell 22 will start to dissolve and the liquid cleansing composition 18 will be able to pass through the shell 22.

In an alternate example, the capsule 10 of FIG. 1 may be made of interlocking outer shell components 12, 14 that are made of pressure-sensitive materials. When such a capsule 10 is exposed to an exterior pressure source (e.g., crushing force applied between the hands of a user), the interlocking outer shell components 12, 14 are ruptured and the liquid cleansing composition 18 is released.

It may be possible that the outer shell material of the capsules 10 of the present invention may be made of materials that have both a water and pressure trigger. Such capsules 10 would release the cleansing composition 18 upon exposure to water, externally applied pressure, or both. One skilled in the art would also see that the different triggers could be used with either of the capsule designs shown in the FIGS. 1 and 2, or with any other capsule designs that are contemplated by this invention.

The liquid cleansing formulation 18 of the present invention is intended for personal cleansing. The composition may be formulated specifically for use on hands, on hair, on the skin, or for any other personal cleansing needs. As such, the composition will contain one or more surfactants appropriate for such purposes. Additionally, the composition may include co-surfactants, therapeutic benefit agents, humectants, emollients, perfumes, colarants, and the like.

Additionally, in an embodiment of the present invention, the liquid cleansing composition 18 may include a foaming agent. Such compositions will self-foam upon release of the composition 18 from the capsule 10. Typically, a propellant gas will be is entrapped within the liquid cleansing composition 18. When released from the confines of the capsule 10, the propellant gas will expand as it is exposed to atmospheric pressure. The expansion of the gas causes the liquid cleansing composition 18 to foam, expanding the volume of the liquid cleansing composition 18. Such an increase in volume provides greater surface area of cleanser available to the consumer and also provides an aesthetically pleasing cleansing experience.

The formulations of the liquid cleansing compositions 18 used in the present invention are commonly aqueous-based. As such, consideration must be made regarding capsules 10 made with shells having a water-based trigger; it is undesirable for the liquid cleansing composition 18 to dissolve the capsule 10 shell materials from the inside and prematurely release the composition 18.

To ensure that the composition 18 contained within the capsule 18 does not trigger the capsule 10 before the capsule 10 is triggered by external exposure to water and/or pressure, a barrier layer 16 may be added to the capsule 10. By supplying the interior of the capsule 10 with a barrier layer 16, the liquid cleansing composition 18 can be kept separated from the outer shell material of the capsule 10, thus preventing unintended release of the liquid cleansing composition 18.

Such a barrier layer 16 is desired to be more adhesive with regard to the capsule 10 than cohesive in nature, such that the barrier layer 16 will stay with the portions of the shell material as the capsule 10 is ruptured or dissolved. It is intended that the barrier layer 16 will not have enough structure itself to contain the liquid cleansing formulation 18 once the capsule 10 has been triggered and capsule structure is compromised.

Generally, such a barrier layer 16 will have a thickness in the range of approximately 10 microns to approximately 250 microns. The thickness may preferably be in the range of approximately 20 microns to approximately 50 microns.

Alternatively to the addition of a barrier layer 16 to the capsule 10, the formulation of the liquid cleansing composition 18 may be modified to self-produce an interfacial barrier layer that separates the shell material and the bulk of the composition 18. A highly hydrophobic surfactant may be balanced within the formulation of the composition 18 such that when placed in a capsule 10 such a surfactant will preferably align at the interface of the aqueous-based liquid cleansing composition 18 and the inner surfaces of the shell 12, 14, 22. This self-formation of a barrier layer within solution will then prevent the bulk of composition 18 from prematurely triggering the release from the capsule 10.

Figure 3:
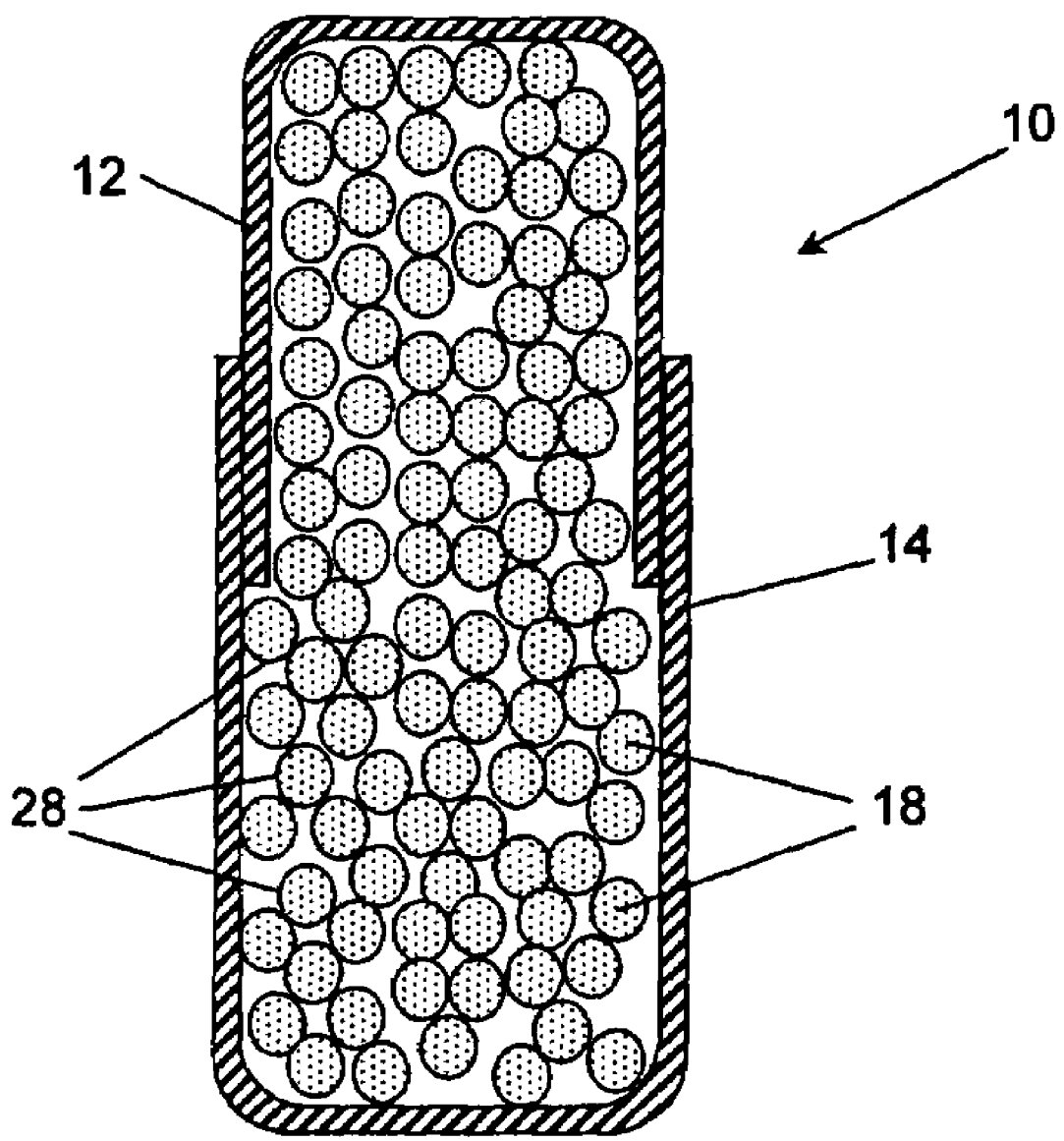
FIG. 3 is a cross sectional view of another interlocking shell capsule embodiment of the present invention.

Another solution to premature triggering of the capsule 10 is shown in the embodiment of FIG. 3. The liquid cleansing composition 10 may be encapsulated into a plurality of micro-capsules 28 that are made from materials that have a trigger of their own. For example, an aqueous-based liquid cleansing composition 18 may be encapsulated in micro-capsules 28 having a pressure sensitive trigger. Such micro-capsules 28 may then be encapsulated within a first and second outer shell 12, 14 components that have a water trigger. Such micro-capsules 28 are substantially spherical in shape and may be in the size range of 100 nm to 3 mm in diameter.

In use, the consumer would trigger the capsule 10, containing the micro-capsules 28, by holding it under water. With the application of water and the agitation of hand-scrubbing, the capsule 10 would be triggered and the micro-capsules 28 would be released from the capsule 10. The micro-capsules 28 could then be triggered by continued hand-scrubbing to then release the liquid cleansing solution 18 contained within the micro-capsules 28.

Capsules 10 may be formed by any of the processes that are well known in the art to encapsulate a composition. Nonlimiting examples of methods of producing capsules include mechanical punching as described in U.S. Pat. No. 6,238,616 to Ishikawa et al., coacervation process as are described in U.S. Pat. No. 4,777,089 to Takizawa et al., U.S. Pat. No. 3,943,063 to Morishita et al. and U.S. Pat. No. 4,978,483 to Redding, Jr.; and by extrusion as discussed in U.S. Pat. No. 3,310,612 to Somerville, Jr.; U.S. Pat. No. 3,389,194 to Somerville; U.S. Pat. No. 2,799,897 to Jansen; U.S. Pat. No. 5,385,737 to Shigeno et al.; and U.S. Pat. No. 5,330,835 to Kikuchi et al. More particularly, the capsules may be manufactured by the methods as disclosed in U.S. patent application Ser. No. 10/954,312 to Reddy et al., filed Sep. 30, 2004, now U.S. Pat. No. 7,258,428.

Figure 4:
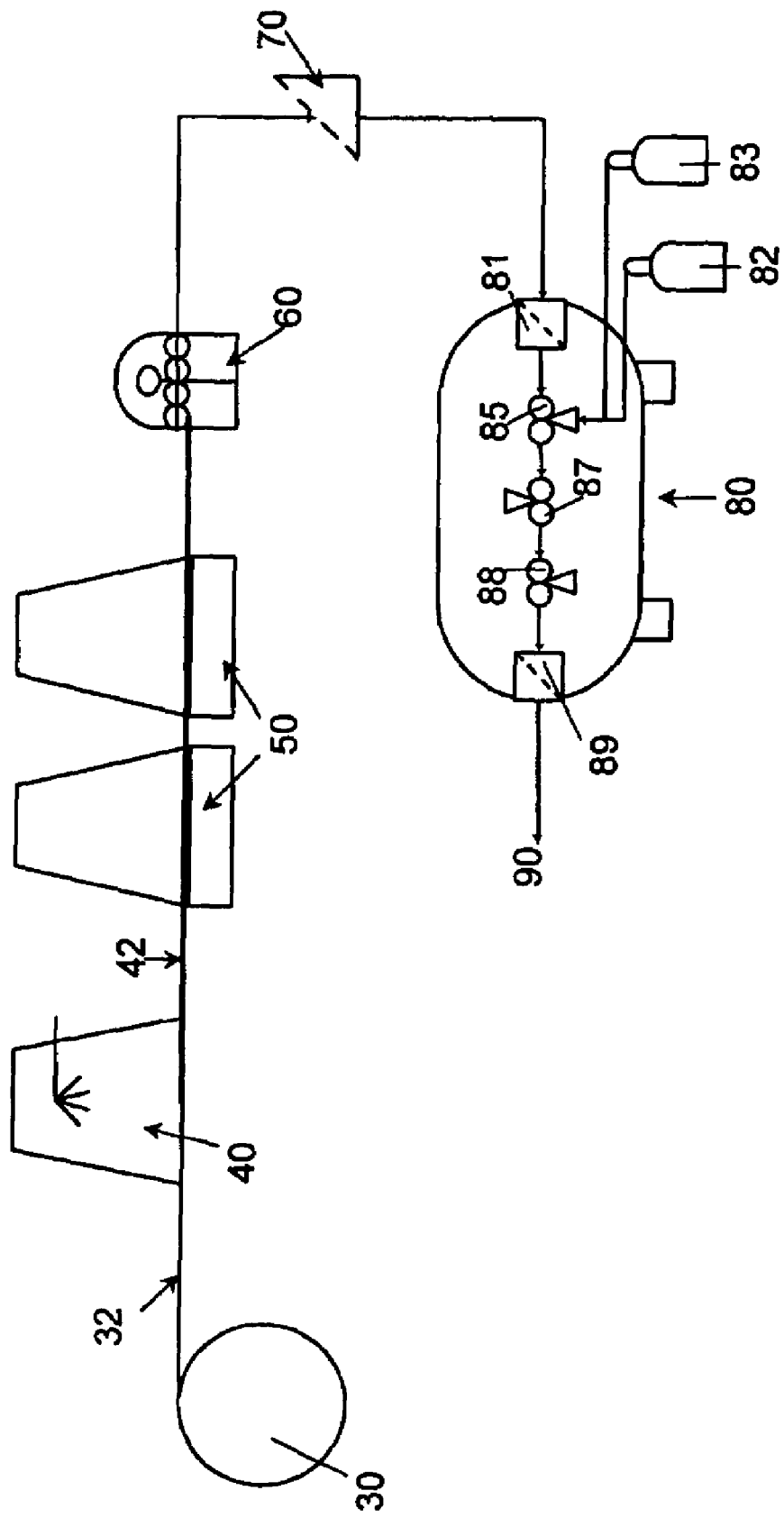
FIG. 4 is a schematic representation of an exemplary encapsulation process for producing the encapsulated liquid cleansing composition capsules of the present invention.

A schematic of a continuous production process that may be used to encapsulate the foaming embodiments of the cleansing compositions of the present invention is shown in FIG. 4. The process illustrated by the schematic of FIG. 4 is a modified mechanical punching-type capsule process using a pressurized enclosure 80 in which the foaming cleaning composition is encapsulated in the capsule shell material. The use of a pressurized enclosure 80 helps stabilize the foaming cleansing composition during encapsulation and ensures that the composition will not start foaming prior to encapsulation.

As shown in FIG. 4, the shell material of the capsule 10 may be provided to the process as a roll 30. The shell material film 32 may alternatively be produced and provided inline with the production process shown. As shown, the shell material film 32 is conveyed to a spray unit 40 where a hydrophobic barrier layer 16 is applied on one side of the shell material film 32. The barrier-coated film 42 is then cured in by a multistage curing process 50. Such curing may be thermal initiated, light initiated, or any other curing initiator as appropriate for the materials being cured, as are known in the art.

A continuous molding apparatus 60 is then used to make the interlocking halves of the capsule shell. The molding is done in such a way that the hydrophobic barrier layer is on the interior of the shell halves. A sorting unit 70 then separates the shell halves.

The shell halves are then conveyed into a pressurized enclosure 80 through an airlock entrance 81. Propellant gas 83 is mixed with the liquid cleansing composition 82 and is injected into the shell halves in the injection unit 85. The filled capsule halves are then joined in an interlocking manner and adhered in the interlocking and adhesive sealing unit 87. An adhesive curing unit 88 then cures the adhesive using heat, UV light, or other curing initiators as appropriate for the particular adhesive being used, as are known in the art. The finished capsules then exit the pressurized enclosure 80 through an airlock exit 89 and proceed in the finished capsule stream 90.

The pressurized enclosure 80 is kept at a pressure sufficient to stabilize the propellant gas 83 being injected into the capsules along with the liquid cleansing composition 82. Likewise, the propellant gas 83 will be regulated to a comparable pressure. Typically, the pressurized enclosure 80 will be greater than the atmospheric pressure outside of the pressurized enclosure 80. Preferably the interior pressure of the pressurized enclosure 80 will be greater than 1 atm (101.3 kPa) and may be up to approximately 2 atm (202.6 kPa). Preferably, the pressurized enclosure 80 will be pressurized to an interior pressure of approximately 10% greater than the atmospheric pressure outside of the pressurized enclosure 80.

Other capsule making processes may be used with such a pressurized enclosure 80 to encapsulate a foaming liquid cleansing formulation. The pressurized enclosure 80 would just need to be used in such a way that the encapsulation of the propellant gas and cleansing formulation occur while both were within the pressurized enclosure 80. Alternatively, the entire capsule making process could be enclosed within such a pressurized enclosure 80 to encapsulate a foaming cleansing composition 18.

The shell materials used to form the bodies of the capsules 10 of the present invention must be compatible with the liquid cleansing composition 18 and/or the barrier layer 16 material to be used with the shell material. Additionally, the capsule 10 must be strong enough to contain the liquid cleansing composition 18 during transport and dispensing of the capsules 10.

Nonlimiting examples of shell materials that may be used in the capsules 10 of the present invention include cellulose, acrylics, vinyls, polyolefins, proteins, guar gum, and the like. Examples of such materials are discussed in greater detail below for exemplary purposes.

Cellulose

Cellulose or cellulose derivatives that are suitable for use in preparing capsules 10 include natural or synthetic substances, such as cellulose, cellulose ester, cellulose ether, cellulose nitrate, cellulose triacetate, cellulose acetate phthate (CAP), methyl cellulose, ethyl cellulose, hydroxypropyl cellulose (HPC), hydroxypropyl methylcellulose (HPMC), and hydroxypropyl methylcellulose phthalate (HPMCP).

The preferred cellulose polymers include hydroxypropyl cellulose (HPC), hydroxypropyl methylcellulose (HPMC), cellulose acetate phthalate (CAP), and hydroxypropylmethylcellulose phthalate (HPMCP). At the present time, at least two grades or types of HPMCP are commercially available from the Shinetsu Chemical Company of Tokyo, Japan. These grades or types are known as HP-50 and HP-55. HP-50 has 20-25% methoxyl content, 8-12% hydroxypropoxyl content, and 20-27% carboxybenzoyl content. HP-55 has 18-22% methoxyl content, 6-10% hydroxylpropoxyl content, and 27-35% carboxybenzoyl content.

Acrylics

The capsules 10 of the present invention may be made of polymer or copolymers of acrylate or acrylate derivatives. The preferred polymers or copolymers of acrylate or acrylate derivative include, but are not limited to, polyacrylate, polymethylacrylate, poly(acrylate-methylacrylate), poly(methacrylate-methylmethacrylate), poly(ethylacrylate-methylmethacrylate), poly(ethylacrylate-methylmethacrylate-trimethylammonioethylmethacrylate chloride), and poly(ethylacrylate-methylmethacrylate-trimethylammonioethylmethacrylate chloride).

For example, the copolymer of methacrylic acid and methacrylic acid alky ester has the following structural unit:

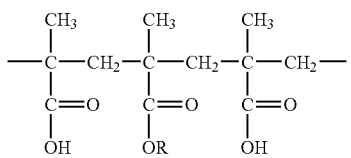

wherein R is a lower alkyl group, in particular, a methyl or ethyl group.

Methacrylic acid/ester copolymer can be prepared according to a number of methods. There are many grades or types of methacrylic acid/ester copolymers that are commercially available. For example, Rohm & Haas Company of Tokyo, Japan, has the so-called Eudragit® series containing various polymethacrylic acid-methacrylic acid copolymer such as Eudragit®-E, L, S, RL, RS, NE. Most of these copolymer are soluble in water when base is added. The preferred Eurdragit® polymer series that may be used in the present invention include Eurdragit®-RS100 and RL-100.

Vinyl

The capsules 10 may be made of vinyl polymers. The preferred vinyl polymers include, but are not limited to, polyvinyl chloride, polyvinyl acetate, polyvinyl alcohol, polystyrene and polyacrylonitrile.

Polyolefins

Polyolefins may be used to make the capsules 10 of the present invention.

Examples of polyolefins include, but are not limited to, polyethylene, polypropylene, and polybutylene.

Proteins

The capsules 10 may be made from proteins. Preferred proteins which may be used in the capsules 10 of the invention are albumen, gelatin, zein, casein, collagen or fibrinogen. Particularly preferred is albumen, either human serum albumen or ovalbumen.

Preferred α-hydroxy acids for use in the invention are glycolic acid, lactic acid, hydroxybutyric acid or mixtures of two or more thereof. Particularly preferred is lactic acid. By α-hydroxy acid derivative is meant an α-hydroxy acid derivatised by conjugation to another molecule, for example, polyethylene glycol.

Process Whey Protein may be used in the capsules 10 of the present invention and are prepared by a procedure in which low molecular weight compounds other than milk whey protein are substantially removed from milk whey which are a waste material from the manufacture of cheese, butter and casein by using milk as the raw material and then the pH of the product is adjusted to not higher than 4 or not lower than 6 and then heat-treated. For example, by using cheese whey formed in the manufacture of cheese, the low molecular weight compounds in milk whey are removed substantially by a dialysis or a chromatography and the product is heat-treated at a pH not higher than 4 or not lower than 6 to give the Process Whey Protein. For example, the method for the preparation of Process Whey Protein is disclosed in U.S. Pat. No. 5,416,196 A and EP 0473270 B, and KINEKAWA, Y. and KITABATAKE, N. "Biosci. Biotech. Biochem." Vol. 51, 834 (1995), KITABATAKE, N., FUJITA, Y. and KINEKAWA, Y. "J. Food Sci." Vol. 61, 500 (1996). The commercial products include "Genesis (trade name)" manufactured by Daiichi-Kasei Co., Ltd of Kyoto, Japan.

Guar Gum

Yet another material for use as the shell material of the capsules 10 of the present invention is gaur gum. More preferably polymeric cationic derivatives of guar gum may be used, and more particularly a polygalactomannan gum may be used. The gum occurs naturally as guar gum, the principal component of the seed of the guar plant, *Cyamopsis tetragonalobus*.

The guar molecule is essentially a straight chain mannan branched at quite regular intervals with single membraned galactose units on alternate mannose units. The mannose units are linked to each other by means of beta (1-4) glycosidic linkages. The galactose branching is accomplished through an alpha (1-6) linkage. The cationic derivatives are obtained by reactions between the hydroxyl groups of the polygalactomannan and reactive quaternary ammonium compounds. The degree of substitution with the cationic groups is desirably at least 0.01 and preferably at least 0.05, for example from 0.08 to 0.5.

Suitable cationic guar gum derivatives are those given the CTFA designation guar hydroxypropyl trimonium chloride, available commercially for example as JAGUAR® C13S, which has a low degree of substitution of the cationic groups, about 0.13, and a high viscosity. The low degree of cationic substitution leads to a cationic charge density of 0.0008. The "cationic charge density" of a polymer, as that term is used in U.S. Pat. No. 3,580,853 to Parran, refers to the ratio of the number of positive charges on a monomeric unit of which the polymer is comprised to the molecular weight of said monomeric unit. The cationic charge density multiplied by the polymer molecular weight determines the number of positively charged active sites of a given polymer chain.

Other suitable guar gum materials include that known as JAGUAR C15, having a moderate degree of substitution and a low viscosity, JAGUAR C17, (high degree of substitution, 0.25-0.31, hence cationic charge density of 0.0016, high viscosity) and JAGUAR C16 which is a hydroxypropylated cationic guar derivative containing a low level of substituent groups as well as cationic quaternary ammonium groups. The degree of substitution of the cationic groups is 0.11-0.16, and the average number of moles of substitution of hydroxypropyl groups is 0.8-1.1. JAGUAR C16 has a cationic charge density of 0.0008. Also suitable is JAGUAR 162 which is a high transparency, medium viscosity guar having a low degree of substitution.

Other shell materials that may be used in the construction of capsules 10 of the present invention may include, albumin, agar-agar, gum arabic, pectins, tragacanth, xanthan, natural and modified starches, dextrans, dextrins, maltodextrin, chitosan, alginates, cellulose derivatives, sugar, glycine, lactose, mannitol, polyvinylpyrrolidone, polyacrylic acid, polymers of methacrylic acid, polymers of methacrylic acid esters, cellulose acetate phthalate, hydroxypropylmethylcellulose phthalate, azo-crosslinked polymethacrylates, polyurethane/sugar copolymers, oligomeric galactomannans, galactomannan derivatives crosslinked with aliphatic diisocyanates, ethylgalactomannans, acetylgalactomannans, polysaccharides crosslinked with adipic acid, lipophilic substances, erodable fatty alcohols; and their mixtures.

Optionally, plasticizers may also be added to the shell polymer formulations used in forming the capsules 10. Such plasticizers may be added to the shell materials to give characteristics to the shell material film that aid in the processing of such materials. Generally, a plasticizer is added to modify viscosity, flexibility, glass transition temperature, strength and the like.

Examples of the plasticizers that are suitable to be used with the shell polymers discussed above include (1) polyglycols such as polypropylene glycol, polybutylene glycol and polyethylene glycol (PEG) (200-6000); (2) organic esters such as diethylphthalate (DEP), dibutylphthalate (DBP), dibutyl sebacate (DBS); (3) citrates such as triethyl citrate (TEC), acetyltriethylcitrate (ATEC), acetyltributylcitrate (ATBC), tributylcitrate (TBC), and triacetyl glycerine (triacetin); and (4) oils/glyerides such as castor oil, acetylated monoglyceride, and purified coconut oil. The preferred plasticizers are polyethylene glycol (e.g., PEG 1000 and 4000), triethyl citrate, tributyl citrate, and triacetin. The preferred amount of plasticizers in the capsule forming compositions is 0%-40% by weight of the capsule, most favorably 0.01% to 20% by weight.

Some polyethylene glycol plasticizers may have the dual function of acting as a barrier layer between the material of the shell and internal composition. Such plasticizers may phase separate under the appropriate process conditions to form a side-specific capsule film materials that can then be converted into finished capsules.

In addition to the materials that are used to make the shell of the capsules 10 of the present invention, other additional materials may be used to aid in the functionality of the capsule 10 or in its construction. Some embodiments of the capsule 10, as discussed above, may include a barrier layer 16 or the use of micro-capsules 28.

The barrier layer 16 of the capsule 10 is a polymer coating inside the material of the shell and in contact with the liquid cleansing compositions. Such a barrier layer 16 may be needed where the capsule 10 is to be triggered by external moisture or liquid that comes in contact with the capsule 10, but where the capsule 10 also contains an aqueous-based cleansing formulation 18. While it is desired that such a capsule 10 be dissolved or ruptured by contact with water (or another liquid) on the outside of the capsule 10, it is also undesirable for the capsule 10 to dissolve from the inside due to the encapsulated liquid cleansing composition 18.

The polymer suitable for use as a barrier layer 16 must be stable in the composition of the liquid cleaning formulation 18 and must disintegrate or dissolve during the rupture of the capsule 10 simply by dilution with water, pH change or mechanical forces such as agitation or abrasion or any other trigger mechanism. The preferred polymers are water soluble or water dispersible polymers that are insoluble, or can be made insoluble, in the liquid cleansing composition 18 of the present invention. Examples of such polymers are described in European Patent 1,390,503 to Craik et al.; U.S. Pat. No. 4,777,089 to Takizawa et al.; U.S. Pat. No. 4,898,781 to Onouchi et al.; U.S. Pat. No. 4,908,233 to Takizawa et al.; and U.S. Pat. No. 5,064,650 to Lew.

These water soluble polymers display an upper consulate temperature or cloud point. As is well known in the art, the solubility or cloud point of such polymers is sensitive to electrolyte and can be "salted out" by the appropriate type and level of electrolyte. Such polymers can generally be efficiently salted out by realistic levels of electrolyte (<10%). Suitable polymers in this class are synthetic nonionic water soluble polymers including: polyvinyl alcohol; polyvinyl pyrrolidone and its various copolymers with styrene and vinyl acetate; and polyacrylamide and its various modification such as those discussed by P. Molyneaux in Water Soluble Polymers CRC Press, Boca Raton, 1984, and by McCormick in Encyclopedia of Polymer Science Vol 17, John Wiley, New York.

Another class of polymers that may be useful as a barrier layer 16 are modified polysaccharides such as carrageenan, guar gum, pectin, xanthan gum, partially hydrolyzed cellulose acetate, hydroxy ethyl, hydroxy propyl and hydroxybutyl cellulose, methyl cellulose and the like. Proteins and modified proteins such as gelatin are still another class of polymers useful in the present invention especially when selected to have an isoelectric pH close to that of the liquid composition in which the polymers are to be employed.

From the discussion above, it is clear that a variety of hydrophilic polymers have potential utility as the barrier layer 16 for the capsules 10 of this invention. The key is to select an appropriate hydrophilic polymer that would be essentially insoluble in the composition (preferably a concentrated liquid system) under the prevailing electrolyte concentration, yet would dissolve or disintegrate when this composition is under conditions of use. The tailoring of such polar polymers is well within the scope of those skilled in the art once the general requirements are known and the principle set forth.

As discussed in the embodiment of FIG. 3, the liquid cleaning composition 18 may be encapsulated in micro-capsules 28 that are themselves contained within a capsule 10. The micro-capsules 28 may be formed by any of the processes that are well known in the art to encapsulate a liquid composition 18 and may be the same type of process as used to produce the capsules 10 or may be a different type of process. Nonlimiting examples of methods of producing capsules include mechanical punching as described in U.S. Pat. No. 6,238,616 to Ishikawa et al., coacervation process as are described in U.S. Pat. No. 4,777,089 to Takizawa et al., U.S. Pat. No. 3,943,063 to Morishita et al. and U.S. Pat. No. 4,978,483 to Redding, Jr.; and by extrusion as discussed in U.S. Pat. No. 3,310,612 to Somerville, Jr.; U.S. Pat. No. 3,389,194 to Somerville; U.S. Pat. No. 2,799,897 to Jansen; U.S. Pat. No. 5,385,737 to Shigeno et al.; and U.S. Pat. No. 5,330,835 to Kikuchi et al. More particularly, the capsules 10 may be manufactured by the methods as disclosed in U.S. patent application Ser. No. 10/954,312 to Reddy et al., filed Sep. 30, 2004, now U.S. Pat. No. 7,258,428.

The micro-capsules 28 may be made of the same type of shell material as the capsule 10 or may be made of a different material. In the case where the micro-capsule 28 is made from a material that is water soluble, a barrier layer 16 similar to the layer discussed for the capsule 10 above may be used on the inside of the micro-capsules 28.

Alternatively, the micro-capsules 28 may be made of a material that is triggered by the application of external pressure. Such materials will initiate release of the liquid cleansing composition 18 upon experiencing a change in pressure experienced by the micro-capsule 28 (i.e., application of pressure or change in atmospheric pressure). Examples of shell materials having a pressure related trigger include aqueous based materials like, poly vinyl alcohols, gelatin and its derivatives, cellulose and its derivatives, starches and their various derivatives, arabic gum, salts of algin, salts of chitin, carrageenan, chitosan and its derivatives.

Other pressure triggered shell materials for use in the micro-capsules 28 may include discontinuous systems such as network structures of poly(methyl methacrylate), poly(butyl methacrylate), poly(hydroxyethyl methacrylate) di- and tri-block copolymers. Additional such discontinuous systems include hydrogels of poly ethylene glycol (PEG).

Another class of pressure triggered shell materials are molten systems. Such molten systems may include waxes (paraffin, crystalline, microcrystalline or a combination thereof in the molecular weight range of 50,000 to 60,000 daltons. Additional examples of useful molten systems would include low density polyethylene (LDPE), high density polyethylene (HDPE), polypropylene, and other types of pressure sensitive plastics such as rubber, latex, and the like.

Any of the above materials either separate or in combination (chemically, physical blend or laminated layers) with each other could act as a material for the micro-capsules 28.

The capsules 10 of the present invention encapsulate liquid cleansing composition 18 until the capsule 10 is ruptured and the liquid cleansing composition 18 released to the user. Such liquid cleaning compositions 18 will contain water with a surfactant. The water used is preferably deionized or distilled water free of dissolved electrolytes such as salts and acids. The surfactants used in the cleansing compositions 18 are those surfactants that are generally known in the art for personal cleansing and are discussed in greater detail below.

Various components may be included to add functionalities to the encapsulated liquid cleansing composition 18 of the invention. Non-limiting examples of components that may be included along with the surfactants may include therapeutic benefit agents, humectants, emollients, perfumes, colarants, and the like. In one specific embodiment of the liquid cleansing compositions 18 encapsulated in the present invention, foaming agents are encapsulated with the cleansing composition 18 to cause the composition 18 to foam when the capsule 10 is ruptured. Specific examples of surfactants, foaming agents, therapeutic benefit and other functional agents that may be included in the encapsulated compositions 18 of the present invention are discussed below and are intended to be exemplary, rather than limiting, in nature.

Surfactants, particularly those characterized as lathering surfactants may be encapsulated for use in the present invention to provide easy and rapid foam generation at surfactants levels desirable to provide skin mildness of the composition.

By a "lathering surfactant" is meant a surfactant, that when combined with water and mechanically agitated generates a foam or lather. It is intended that such a capsule 10 containing encapsulated lathering surfactants would be used with a water source. These surfactants should be mild, which means that they provide sufficient cleansing or detersive benefits but do not overly dry the skin or hair (e.g., removing too much natural oil and/or moisture).

The surfactant component of the liquid cleansing composition 18 constitutes about 5-40%, preferably about 10-25% by weight of the cleaning composition.

A wide variety of lathering surfactants are useful herein and include those selected from the group consisting of anionic lathering surfactants, nonionic lather surfactants, amphoteric lathering surfactants, and mixtures thereof. Generally, the lathering surfactants do not strongly interfere with deposition of any skin care active and, or conditioning agents that are present, e.g., are fairly water soluble, and usually have an HLB value of above 10. Cationic surfactants can also be used as optional components, provided they do not negatively impact the overall lathering characteristics of the required lathering surfactants. Additionally, co-surfactants may be present in the liquid cleansing composition, as stabilizers.

Anionic Lathering Surfactants

A wide variety of anionic lathering surfactants are useful as encapsulated liquid cleansing composition 18 of the present invention. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulas ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

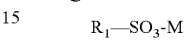

$$R_1\text{—}SO_3\text{-}M$$

wherein $R_1$ is chosen from the group consisting of a straight or branched chain, saturated aliphatic hydrocarbon radical having from about 8 to about 24, alternatively about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids, typically having from about 8 to about 24 carbon atoms, alternatively from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853 to Collins.

Other anionic materials include phosphates such as monoalkyl, dialkyl, and trialkylphosphate salts.

Other anionic materials include alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates that are based on taurine, which is also known as 2-aminoethanesulfonic acid. Especially useful are taurates having carbon chains between C$_8$ and C$_{16}$. Examples of taurates include N-alkyltaurines such as the one prepared by reacting dodecylamine with sodium isethionate according to the teaching of U.S. Pat. No. 2,658,072 to Kosmin. Further nonlimiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between C$_8$ and C$_{16}$. Nonlimiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between C$_8$ and C$_{16}$. Nonlimiting examples of glutamates include ammonium, sodium, potassium and alkanolamine (e.g., triethanolamine) salts of lauroyl glutamate, myristoyl glutamate, and cocoyl glutamate.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Other known anionic lathering surfactants useful in the encapsulated liquid cleansing composition 18 of the present invention may be found in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al.

Nonionic Lathering Surfactants

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Alkyl glucosides and alkyl polyglucosides are useful herein, and can be broadly defined as condensation articles of long chain alcohols, e.g. $C_{8-30}$ alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

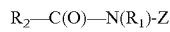

$R_2$—C(O)—N($R_1$)-Z wherein: $R_1$ is H, $C_1$-$C_4$ alkyl, 2-hydroxyethyl, 2-hydroxypropyl, alternatively $C_1$-$C_4$ alkyl, more alternatively methyl or ethyl, most alternatively methyl; $R_2$ is $C_5$-$C_{31}$ alkyl or alkenyl, alternatively $C_7$-$C_{19}$ alkyl or alkenyl, more alternatively $C_9$-$C_{17}$ alkyl or alkenyl, most alternatively $C_{11}$-$C_{15}$ alkyl or alkenyl; and Z is a polhydroxyhydrocarbyl moiety having a linear hydrocarbyl chain with a least 3 hydroxyls directly connected to the chain, or an alkoxylated derivative (alternatively ethoxylated or propoxylated) thereof. Z alternatively is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R_2CO$— moiety is derived from coconut oil fatty acids). Processes for making compositions containing polyhydroxy fatty acid amides are disclosed, for example, in U.S. Pat. No. 2,965,576 to Wilson; U.S. Pat. No. 2,703,798 to Schwartz; and U.S. Pat. No. 1,985,424 to Piggott.

Other examples of nonionic surfactants include amine oxides. Amine oxides correspond to the general formula $R_1R_2R_3N\rightarrow O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in the capsules of this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide, and mixtures thereof.

Other known examples of nonionic lathering surfactants for use in the encapsulated liquid cleansing composition 18 of present invention are discussed in McCutcheon's, Detergents and Emulsifiers, North American edition (1986), published by allured Publishing Corporation; and McCutcheon's, Functional Materials, North American Edition (1992).

Amphoteric Lathering Surfactants

The term "amphoteric lathering surfactant," as used herein, is also intended to encompass zwitterionic surfactants, which are well known to formulators skilled in the art as a subset of amphoteric surfactants. A wide variety of amphoteric lathering surfactants can be used in the encapsulated liquid cleansing composition 18 of the present invention. Particularly useful are those which are broadly described as derivatives of aliphatic secondary and tertiary amines, alternatively wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza, Inc. of Allendale, N.J.), lauryl bis-(2-hydroxyethyl) carboxymethyl betaine, oleyl di-methyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc of Cranbury, N.J.).

Preferred for use herein are amphoteric surfactants having the following structure:

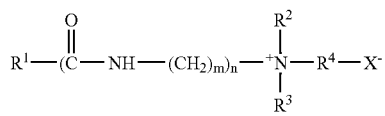

wherein $R_1$ is unsubstituted, saturated or unsaturated, straight or branched chain alkyl having from about 9 to about 22 carbon atoms. Preferred $R_1$ has from about 11 to about 18 carbon atoms; more alternatively from about 12 to about 18 carbon atoms; more alternatively still from about 14 to about 18 carbon atoms; m is an integer from 1 to about 3, more alternatively from about 2 to about 3, and more alternatively about 3; n is either 0 or 1, alternatively 1; $R_2$ and $R_3$ are independently selected from the group consisting of alkyl having from 1 to about 3 carbon atoms, unsubstituted or mono-substituted with hydroxy, preferred $R_2$ and $R_3$ are $CH_3$; X is selected from the group consisting of $CO_2$, $SO_3$ and $SO_4$; $R_4$ is selected from the group consisting of saturated or unsaturated, straight or branched chain alkyl, unsubstituted or monosubstituted with hydroxy, having from 1 to about 5 carbon atoms. When X is $CO_2$, $R_4$ alternatively has 1 or 3 carbon atoms, more alternatively 1 carbon atom. When X is $SO_3$ or $SO_4$, $R_4$ alternatively has from about 2 to about 4 carbon atoms, more alternatively 3 carbon atoms.

Examples of amphoteric surfactants of the encapsulated liquid cleansing composition of the present invention include the following compounds: cetyl dimethyl betaine (this material also has the CTFA designation cetyl betaine), wherein R has from about 9 to about 13 carbon atoms; and cocamidopropyl hydroxy sultaine, wherein R has from about 9 to about 13 carbon atoms, Examples of other useful amphoteric surfactants are alkyliminoacetates, and iminodialkanoates and aminoalkanoates of the formulas $RN[(CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 to Lynch; and the products sold under the trade name "Miranol" and described in U.S. Pat. No. 2,528,378 to Mannheimer. Other examples of useful amphoterics include amphoteric phosphates, such as coamidopropyl PG-dimonium chloride phosphate (commercially available as Monaquat PTC, from Mona Industries of Paterson, N.J.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Other known examples of amphoteric surfactants useful in the encapsulated liquid cleansing composition 18 of the present invention are disclosed in McCutcheon's, Detergents and Emulsifiers, North American edition (1986), published by allured Publishing Corporation; and McCutcheon's, Functional Materials, North American Edition (1992).

Co-Surfactants

The encapsulated cleansing liquid cleansing composition 18 of the present invention may optionally contain one or more co-surfactants as stabilizers for the encapsulated cleansing compositions. Ideally, the co-surfactants will contribute to the cleansing and lathering capabilities of the resultant composition, but is not a requirement of their stabilizing function. Preferably, these co-surfactants will also be lathering surfactants and may be selected from the group consisting of anionic lathering surfactants, nonionic lathering surfactants, cationic lathering surfactants, amphoteric lathering surfactants, and combinations thereof.

Nonlimiting examples of anionic lathering surfactants useful as stabilizing co-surfactants in the encapsulated liquid cleansing composition of the present invention are disclosed in U.S. Pat. No. 3,929,678 to Laughlin et al. A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof.

Nonlimiting examples of nonionic lathering surfactants for use as stabilizing co-surfactants in the encapsulated liquid cleansing composition of the present invention include those selected from the group consisting of alkyl glucosides, alkyl polyglucosides, polyhydroxy fatty acid amides, alkoxylated fatty acid esters, sucrose esters, amine oxides, and mixtures thereof.

Nonlimiting examples of cationic lathering surfactants for use as stabilizing co-surfactants in the encapsulated liquid cleansing composition of the present invention include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate. The fatty amines, however, are preferred. It is preferred that a lather booster is used when the cationic lathering surfactant is the primary lathering surfactant of the cleansing component. Additionally, nonionic surfactants have been found to be particularly useful in combination with such cationic lathering surfactants.

Nonlimiting examples of amphoteric or zwitterionic surfactants for use as stabilizing co-surfactants in the encapsulated liquid cleansing composition of the present invention are those selected from the group consisting of betaines, sultaines, hydroxysultaines, alkyliminoacetates, iminodialkanoates, aminoalkanoates, and mixtures thereof.

Another possible ingredient of the liquid cleaning composition 18 are foaming additives. Foaming additives are essential for the self-foaming cleansing composition embodiments of the present invention. The foaming additive is preferably a hydrocarbon, in a gaseous state, selected from the group consisting of n-pentane, isopentane, neopentane, n-butane, and isobutane, and mixtures thereof. A blend of isopentane and isobutane in a weight ratio of 9:2 is particularly desirable. Such propellant gasses are present in the amount of about 0.1-15% by weight, and preferably about 1-7% within the liquid composition mixture.

Another ingredient may be fluorosurfactants or fluorinated surfactants which are widely used in the manufacture of fluoropolymers (and copolymers) in aqueous media. While the addition of the propellant gas will cause any aqueous-based surfactant cleansing composition 18 to foam upon release from the capsule 10, the use of a fluorinated surfactant will cause the cleansing composition 18 to foam to an even greater degree (i.e., increase in volume to a greater degree).

Though chiefly used in the manufacture of fluoropolymer dispersions and the dry, solid polymers derived therefrom, they are also commonly employed in the manufacture of slurry-(or granular-) type polymer as well, as described, for example, for the polymerization of tetrafluoroethylene (TFE) in U.S. Pat. No. 3,245,972 to Anderson et al.; U.S. Pat. No. 3,629,219 to Esker; U.S. Pat. No. 3,855,191 to Doughty, Jr. et al.; and U.S. Pat. No. 4,189,551 to Gangal. Chief among the fluorinated surfactants generally used are perfluoroalkanoates, especially perfluorooctanoate, usually in the form of the ammonium salt (APFO), although alkali metal salts and even the corresponding free acid may alternatively be used.

Commercially available fluorinated surfactants include Zonyl FSA, an anionic fluorochemical surfactant manufactured by E.I. DuPont de Nemours & Company (Wilmington, Del.); Zonyl FSK, an amphoteric fluorochemical surfactant manufactured by E.I. DuPont de Nemours & Company; Zonyl FSN, a nonionic fluorochemical surfactant manufactured by E.I. DuPont de Nemours & Company; and Lodyne S-112B, a blend of an anionic fluorochemical sodium sulfonate type and a nonionic fluorochemical synergist of the fluoroalkyl amide type manufactured by Ciba-Geigy (Toms River, N.J.).

The encapsulated liquid cleansing composition 18 may optionally contain a safe and effective amount of therapeutic benefit agent such as vitamin compounds, skin treating agents, anti-acne actives, anti-wrinkle actives, anti-skin atrophy actives, anti-inflammatory actives, topical anesthetics, artificial tanning actives and accelerators, anti-microbial actives, anti-fungal actives, sunscreen actives, anti-oxidants, skin exfoliating agents, and combinations thereof.

As used herein, "a safe and effective amount" means an amount of a compound or component sufficient to significantly induce a positive effect or benefit, but low enough to avoid serious side effects, (e.g., undue toxicity or allergic reaction), i.e., to provide a reasonable benefit to risk ratio, within the scope of sound medical judgment. The amount of therapeutic benefit agent present in the liquid cleansing compositions 18 will vary by the specific, individual agent, but all such agents, if present, will be present in an amount of approximately 0.01% to about 15% by weight of the liquid cleansing composition 18.

The optional components useful herein can be categorized by their therapeutic or aesthetic benefit or their postulated mode of action. It is to be understood, however, that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

Vitamin Compounds

The encapsulated liquid cleansing composition 18 may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

In particular, the encapsulated liquid cleansing composition of the present invention may comprise a safe and effective amount of a vitamin B3 compound. Vitamin B3 compounds are particularly useful for regulating skin condition as described in U.S. Pat. No. 6,238,678 to Oblong. The encapsulated liquid cleansing composition of the present invention preferably comprise from about 0.01% to about 15% by weight of the composition, more preferably from about 0.1% to about 10%, even more preferably from about 0.5% to about 10%, and still more preferably from about 1% to about 5%, most preferably from about 2% to about 5%, of the vitamin B3 compound.

As used herein, "vitamin B3 compound" means a compound having the formula:

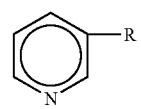

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Skin Treating Agents

The encapsulated liquid cleansing composition 18 of the present invention may contain one or more skin treating agents. Suitable skin treating agents include those effective for preventing, retarding, arresting, and/or reversing skin wrinkles. Examples of suitable skin treating agents include, but are not limited to, alpha-hydroxy acids such as lactic acid and glycolic acid and beta-hydroxy acids such as salicylic acid.

Anti-Acne Actives

Examples of useful anti-acne actives for the encapsulated liquid cleansing composition 18 of the present invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of anti-wrinkle and anti-skin atrophy actives useful for the encapsulated liquid cleansing composition 18 of the present invention include, but are not limited to, retinoic acid and its derivatives (e.g., cis and trans); retinol; retinyl esters; niacinamide, salicylic acid and derivatives thereof; sulfur containing D and L amino acids and their derivatives and salts, particularly the N-acetyl derivatives, a preferred example of which is N-acetyl-L-cysteine; thiols, e.g., ethane thiol; hydroxy acids, phytic acid, lipoic acid; lysophosphatidic acid, and skin peel agents (e.g., phenol and the like).

Non-Steroidal Anti-inflammatory Actives (NSAIDS)

Examples of NSAIDS useful for the encapsulated liquid cleansing composition 18 of the present invention include, but are not limited to, the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics

Examples of topical anesthetic drugs useful for the encapsulated liquid cleansing composition 18 of the present invention include, but are not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Actives and Accelerators

Examples of artificial tanning actives and accelerators useful for the encapsulated liquid cleansing composition 18 of the present invention include, but are not limited to, dihydroxyacetaone, tyrosine, tyrosine esters such as ethyl tyrosinate, and phospho-DOPA.

Antimicrobial and Antifungal Actives

Examples of antimicrobial and antifungal actives useful for the encapsulated liquid cleansing 18 composition of the present invention include, but are not limited to, β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Anti-Viral Agents

The encapsulated liquid cleansing composition 18 of the present invention may further comprise one or more anti-viral agents. Suitable anti-viral agents include, but are not limited to, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in U.S. Pat. No. 6,294,186 to Beerse et al.

Enzymes

The encapsulated liquid cleansing composition 18 of the present invention may optionally include one or more enzymes. Preferably, such enzymes are dermatologically acceptable. Suitable enzymes include, but are not limited to, keratinase, protease, amylase, subtilisin, etc.

Sunscreen Actives

The encapsulated liquid cleansing composition 18 may also include sunscreening actives. Nonlimiting examples of sunscreens which are useful in the encapsulated compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl)methylaminobenzoic acid ester with 4-hydroxydibenzoylmethane, 4-N, N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy)dibenzoylmethane, and mixtures thereof. Exact amounts of sunscreens which can be employed will vary depending upon the sunscreen chosen and the desired Sun Protection Factor (SPF) to be achieved.

A wide variety of known sunscreening agents are also described in U.S. Pat. No. 5,087,445 to Haffey et al.; U.S. Pat. No. 5,073,372 to Turner et al.; and U.S. Pat. No. 5,073,371 to Turner et al. Still other useful sunscreens are those disclosed in U.S. Pat. No. 4,937,370 to Sabatelli and U.S. Pat. No. 4,999,186, to Sabatelli et al.

Hydrocolloids

Hydrocolloids may also be optionally included in the encapsulated composition 18 of the present invention. Hydrocolloids are well known in the art and are helpful in extending the useful life of the surfactants contained in the encapsulated liquid cleansing composition 18 of the present invention such that the articles may last throughout at least one entire showering or bathing experience. Suitable hydrocolloids include, but are not limited to, xanthan gum, carboxymethyl cellulose, hydroxyethyl cellulose, hydroxylpropyl cellulose, methyl and ethyl cellulose, natural gums, gudras guar gum, bean gum, natural starches, deionitized starches (e.g., starch octenyl succinate) and the like.

Exothermic Zeolites

Zeolites and other compounds which react exothermically when combined with water may also be optionally included in the encapsulated liquid cleansing composition 18 of the present invention.

Hydrogel Forming Polymeric Gelling Agents

In certain embodiments of the present invention, the liquid cleansing composition 18 may optionally comprise an aqueous gel, i.e., a "hydrogel", formed from a hydrogel forming polymeric gelling agent and water. More specifically, the hydrogel is contained within the cleansing component or the therapeutic benefit component of the article.

Suitable hydrogel forming polymeric gelling agents in the form of particles are commercially available from Hoechst Celanese Corporation, Portsmouth, Va., USA (Sanwet® Superabsorbent Polymers) Nippon Shokubai, Japan (Aqualic®, e.g., L-75, L-76) and Dow Chemical Company, Midland, Mich., USA (Dry Tech®). Hydrogel forming polymeric gelling agents in the form of fibers are commercially available from Camelot Technologies Inc., Leominster, Mass., USA (Fibersorb®, e.g., SA 7200H, SA 7200M, SA 7000L, SA 7000, and SA 7300).

Chelators

The encapsulated composition 18 of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the encapsulated liquid cleansing composition of the subject invention, preferably from about 0.1% to about 10% by weight of the composition, more preferably from about 1% to about 5%, of the composition. Exemplary chelators that are useful herein are disclosed in U.S. Pat. No. 5,487,884 to Bissett et al.; U.S. Pat. No. 5,462,963 to Bush et al., and U.S. Pat. No. 5,364,617 to Bush et al. Preferred chelators useful in encapsulated liquid cleansing composition of the subject invention are furildioxime and derivatives thereof.

Flavonoids

The encapsulated liquid cleansing composition 18 of the present invention may optionally comprise a flavonoid compound. Flavonoids are broadly disclosed in U.S. Pat. No. 5,686,082 to N'Guyen, U.S. Pat. No. 5,686,367 Hayashi, and U.S. Pat. No. 6,093,411 to Bissett. Favonoid compounds may be present in the encapsulated liquid cleansing compositions at concentrations of from about 0.01% to about 15% by weight of the composition, more preferably from about 0.1% to about 10%, and most preferably from about 0.5% to about 5%.

Sterols

The encapsulated liquid cleansing composition 18 of the present invention may comprise a safe and effective amount of one or more sterol compounds. Examples of useful sterol compounds include sitosterol, stigmasterol, campesterol, brassicasterol, lanosterol, 7-dehydrocholesterol, and mixtures thereof. These can be synthetic in origin or from natural sources, e.g., blends extracted from plant sources (e.g., phytosterols).

Anti-Cellulite Agents

The encapsulated liquid cleansing composition of the present invention may also comprise a safe and effective amount of an anti-cellulite agent. Suitable agents may include, but are not limited to, xanthine compounds (e.g., caffeine, theophylline, theobromine, and aminophylline).

Skin Lightening Agents

The encapsulated liquid cleansing composition 18 of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof, e.g., magnesium ascorbyl phosphate or sodium ascorbyl phosphate or other salts of ascorbyl phosphate. Skin lightening agents suitable for use herein also include those described in U.S. Ser. No. 08/479,935 to Hillebrand, filed on Jun. 7, 1995, now abandoned; and U.S. Pat. No. 6,068,836 to Kvalnes et al.

Hydrophobic Conditioning Agents

The encapsulated liquid cleansing composition 18 of the present invention may comprise one or more hydrophobic conditioning agents which are useful for providing a conditioning benefit to the skin and/or hair during use.

The hydrophobic conditioning agent may be selected from one or more hydrophobic conditioning agents such that the weighted arithmetic mean solubility parameter of the hydrophobic conditioning agent is less than or equal to 10.5.

Nonlimiting examples of hydrophobic conditioning agents include those selected from the group consisting of mineral oil, petrolatum, lecithin, hydrogenated lecithin, lanolin, lanolin derivatives, $C_7$-$C_{40}$ branched chain hydrocarbons, $C_1$-$C_{30}$ alcohol esters of $C_1$-$C_{30}$ carboxylic acids, $C_1$-$C_{30}$ alcohol esters of $C_2$-$C_{30}$ dicarboxylic acids, monoglycerides of $C_1$-$C_{30}$ carboxylic acids, diglycerides of $C_1$-$C_{30}$ carboxylic acids, triglycerides of $C_1$-$C_{30}$ carboxylic acids, ethylene glycol monoesters of $C_1$-$C_{30}$ carboxylic acids, ethylene glycol diesters of $C_1$-$C_{30}$ carboxylic acids, propylene glycol monoesters of $C_1$-$C_{30}$ carboxylic acids, propylene glycol diesters of $C_1$-$C_{30}$ carboxylic acids, $C_1$-$C_{30}$ carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol $C_4$-$C_{20}$ alkyl ethers, di-$C_8$-$C_{30}$ alkyl ethers, and combinations thereof.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the $C_7$-$C_{40}$ isoparaffins, which are $C_7$-$C_{40}$ branched hydrocarbons. Polydecene, a branched liquid hydrocarbon, is also useful herein and is commercially available under the trade names Puresyn 100® and Puresyn 3000® from Mobile Chemical (Edison, N.J.).

Also useful are various $C_1$-$C_{30}$ monoesters and polyesters of sugars and related materials. Suitable ester materials are further described in, U.S. Pat. No. 2,831,854 Tucker et al., U.S. Pat. No. 4,005,196 to Jandacek et al.; U.S. Pat. No. 4,005,195 to Jandacek; U.S. Pat. No. 5,306,516, to Letton et al.; U.S. Pat. No. 5,306,515 to Letton et al.; U.S. Pat. No. 5,305,514 to Letton et al.; U.S. Pat. No. 4,797,300 to Jandacek et al.; U.S. Pat. No. 3,963,699 to Rizzi et al.; U.S. Pat. No. 4,518,772 to Volpenhein; and U.S. Pat. No. 4,517,360 to Volpenhein.

Nonvolatile silicones such as polydialkylsiloxanes, polydiarylsiloxanes, and polyalkarylsiloxanes are also useful oils. These silicones are disclosed in U.S. Pat. No. 5,069,897 to Orr. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by GE Silicones, of Wilton, Conn. and the Dow Corning® series sold by Dow Corning Corporation of Midland, Mich. Specific examples of polydimethylsiloxanes useful herein include Dow Corning® 225 fluid having a viscosity of 10 centistokes and a boiling point greater than 200 degrees C., and Dow Corning® 200 fluids having viscosities of 50, 350, and 12,500 centistokes, respectively, and boiling points greater than 200 degrees C. Also useful are materials such as trimethylsiloxysilicate, which is a polymeric material corresponding to the general chemical formula $[(CH_3)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25 degrees C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810® ($C_{24}$-$C_{28}$ alkyl methicone) (sold by Goldschmidt) and SF1632 (cetearyl methicone)(sold by General Electric Company).

Vegetable oils and hydrogenated vegetable oils are also useful herein.

Also useful are $C_4$-$C_{20}$ alkyl ethers of polypropylene glycols, $C_1$-$C_{20}$ carboxylic acid esters of polypropylene glycols, and di-$C_8$-$C_{30}$ alkyl ethers. Nonlimiting examples of these materials include PPG-14 butyl ether, PPG-15 stearyl ether, dioctyl ether, dodecyl octyl ether, and mixtures thereof.

Hydrophilic Conditioning Agents

The encapsulated liquid cleansing composition 18 of the present invention may optionally comprise one or more hydrophilic conditioning agents as therapeutic benefit agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated $C_3$-$C_6$ diols and triols, alpha-hydroxy $C_2$-$C_6$ carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the encapsulated liquid cleansing composition 18 of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953 to Orr et al.

Preferred cleansing compositions 18 that include therapeutic benefit agents are in the form of an emulsion, which further comprises an aqueous phase and an oil phase. As will be understood by the skilled artisan, a given component will distribute primarily into either the aqueous or oil phase, depending on the water solubility/dispersibility of the therapeutic benefit agent in the component. In one embodiment, the oil phase comprises one or more hydrophobic conditioning agents. In another embodiment, the aqueous phase comprises one or more hydrophilic conditioning agents.

Structured Conditioning Agents

The encapsulated therapeutic benefit agents of the present invention may be structured conditioning agents. Suitable structured conditioning agents include, but are not limited to, vesicular structures such as ceramides, liposomes, and the like.

In another embodiment, the therapeutic benefit agents are comprised within a coacervate-forming composition. Preferably, the coacervate-forming composition comprises a cationic polymer, an anionic surfactant, and a dermatologically acceptable carrier for the polymer and surfactant.

Additionally, the liquid cleansing composition 18 may also include other agents that add functionalities and aesthetic enhancement to the composition. Such functional agents are common in such cleansing formulations and are well known. Non-limiting examples include humectants (to help the skin remain moist), emollients (to help maintain the soft, smooth, and pliable appearance of the skin and to otherwise help improve the skin's appearance), perfumes (to provide pleasing scents), colorants (to impart color to the composition), preservatives (to prevent microbial contamination and growth) and the like.

EXAMPLES

The invention is further described with reference to the following detailed examples, which illustrate several liquid cleansing compositions that may be encapsulated in various types of capsules to form various embodiments of the present invention. The examples are included for illustrative purposes and should not be construed as limiting the invention.

Example 1

The inside of a gelatin capsule of standard size 12 (0.6 inches×1.6 inches; 15 mm×41 mm) was coated with a fine mist of molten microcrystalline wax (MULTIWAX® W-445 from Chemtura Corporation, Middlebury, Conn.). The gelatin capsule with the wax barrier layer was then filed with about 5 ml of an aqueous cleansing formulation. The cleansing formulation was released from the capsule upon exposure of the capsule to water.

The aqueous antimicrobial liquid cleansing formulation used was as described in U.S. Pat. No. 5,837,274 to Shick et al. and given below:

| INGREDIENT | Percent Composition (Broad Range) | Percent Composition (Narrower Range) |
|---|---|---|
| WATER PHASE | | |
| Deionized water | 20.0 to 75.0 | 25.0 to 35.0 or as required |
| Ucare JR 400 | 0.05 to 0.5 | 0.1 to 0.25 |
| SURFACTANT PHASE | | |
| Miracare MS-1 | 20.0 to 50.0 | 40.0 to 50.0 |
| Standamox CAW | 2.0 to 10.0 | 4.0 to 6.0 |
| Topicare PP-15 | 0.5 to 5.0 | 1.0 to 3.0 |
| Amercil 357 | 0.0 to 1.0 | 0.0 to 1.0 |
| PRESERVATIVE PHASE | | |
| Glycerine | 1.0 to 10.0 | 5.0 to 10.0 |
| DMDM Hydantoin | 0.4 or as needed | 0.4 or as needed |
| Tetrasodium EDTA | 0.1 or as needed | 0.1 or as needed |
| ACTIVE PHASE | | |
| Triclosan | 0.1 to 1.0 | 0.5 to 1.0 |
| Tween 40 | 1.0 to 5.0 | 1.0 to 3.0 |
| Fragrance | 0.0 to 0.3 | 0.0 to 0.1 |

Example 2

A capsule could be made with a shell of water soluble PVA films commercially available from Dalian BHY Water Soluble Film Co., Ltd of Dailan, China. Such capsules could be used along with a film barrier coating made of propylene glycol solution and elaborated in U.S. Pat. No. 4,898,781 to Onouchi et al.

Capsules could be made having a 0.6-inch diameter (15 mm) and a length of 1.6 inches (41 mm) (Standard size 12) shells could be made from process as described in our invention or traditional technologies as described in U.S. Pat. No. 6,238,626 to Higuchi et al. The capsules could then be filled with an aqueous cleanser formulation as described in U.S. Pat. No. 5,910,455 to Maddern et al. and as given below:

| | % by weight |
|---|---|
| Blend of paramenthadienes (TABS DS terpene mixture) | 7.00 |
| PPG-2 Methyl Ether | 4.00 |
| PPG-1-PEG-9 Lauryl Glycol Ether | 6.00 |
| PEG-40 Hydrogenated Castor Oil | 6.00 |
| Phenoxyethanol | 0.16 |
| Methyldibromo Glutaronitrile | 0.04 |
| *Aloe Barbadensis* Gel | 0.01 |
| Parfum (Orange citrus fragrance) | 1.40 |
| Aqua (water) | 75.39 or as needed |

Example 3

The gelatin capsules could be color coded like the ones available from Capsuline, Inc., Pompano Beach, Fla. Standard size 0 (0.3 inches×0.85 inches; 7.6 mm×21.6 mm) capsule could be internally spray coated with a fine mist of molten microcrystalline wax, such as MULTIWAX® W-445 from Chemtura Corporation, Middlebury, Conn. Approximately, 0.35 ml of concentrated aqueous cleanser formulation could be injected with commercially available equipment. Such an aqueous cleanser formulation may be as described in U.S. Pat. No. 6,432,429 to Maddern et al. and as given below:

| | % by weight |
|---|---|
| Octyl Cocoate | 3.0 |
| Propylene glycol | 3.0 |
| C11-15 Pareth-5 | 3.0 |
| Sodium Pyrrolidone Carboxylate (50% by weight aqueous solution) | 1.0 |
| Sodium Laureth-11 Carboxylate (22% by weight aqueous solution) | 2.5 |
| Methylparaben | 0.1 |
| Propylparaben | 0.1 |
| Quaternium-15 | 0.2 |
| Water | up to 100 |

Example 4

The gel capsule may be extruded in the form of a one piece gelatin capsules 0.39 inches (9.9 mm) in diameter and 1.03 inches (262 mm) long (standard capsule size 000) as described in U.S. Pat. No. 4,263,251 to Voegle.

The composition of the shell material could be as given below:

| | % by weight |
|---|---|
| Gelatin | 54% |
| Glycerin | 22% |
| Glycerol | 8% |
| Anidrisorb ® 35/70 | 10% |
| Water | 5% |
| Dye | 0.5% |
| BHT (antioxidant) | 0.1% |

Such a capsule could be made without the use of a barrier layer on the inside of the capsule. The composition of the aqueous cleanser formulation could be balanced such that the surfactants used in the compositions would form a interfacial barrier between the bulk of the composition and the shell wall.

An aqueous cleanser formulation that may be encapsulated and incorporated into the wiper as described is also described in U.S. Pat. No. 6,432,429 to Maddern et al. and is given below:

|  | % by weight |
| --- | --- |
| PPG-1n-Propyl Ether | 4.0 |
| D-Limonene (Dipentene) | 7.0 |
| Alcohol ethoxylate (OE 7) | 4.0 |
| PEG-200 Hydrogenated Glyceryl Palmitate and PEG-7 Glyceryl Cocoate (blend) | 3.0 |
| Methyl Paraben | 0.2 |
| Propyl Paraben | 0.1 |
| Quaternium 15 | 0.1 |
| Tocopheryl acetate | 0.1 |
| B.H.A | 0.02 |
| Water | up to 100 |

Example 5

A gelatin capsule of standard size 1, containing about 0.5 grams of micro-capsules, each encapsulating a cleaning formulation. Each of the micro-capsules may be 1 mm in diameter and may be manufactured by the methods as disclosed in U.S. patent application Ser. No. 10/954,312 to Reddy et al., filed Sep. 30, 2004, now U.S. Pat. No. 7,258,428. Such wax micro-capsules may be made of a commercially available pressure-sensitive microcrystalline wax, such as MULTI-WAX® W-445 from Chemtura Corporation, Middlebury, Conn.

An example of a cleansing formulation that may be encapsulated in the micro-capsules contained within the gelatin capsule may be as described in U.S. Pat. No. 6,806,213 to Brooks, and as given below:

| Class | Compound | Percent (%) |
| --- | --- | --- |
| Deionized water |  | 96.9975 |
| Solubilizing agent | Propylene glycol | 1.5 |
| Preservative | GLYDANT PLUS | 0.3 |
| Mild surfactant | MACKAM 2C | 0.5 |
| Moisturizer | Glycerin | 0.4 |
| Skin vitamin | MIRACARE SML E/5 | 0.01 |
| Aloe | Aloe | 0.0025 |
| Fragrance | Fragrance | 0.06 |
| Solubilizing agent | Polysorbate 20 | 0.23 |

Alternatively, the micro-capsules may be 1.5 mm in diameter and 0.4 grams of such micro-capsules may be used in the capsule. In another embodiment, the capsule may be filled with 0.6 grams of micro-capsules having a diameter of 2 mm.

Example 6

A pressure-sensitive, interlocking gelatin capsule of standard size 7 (0.9-inch dia.×3.1 inches; 15 mm×79 mm) could be coated with a fine mist of molten microcrystalline wax, such as MULTIWAX® W-445 from Chemtura Corporation, Middlebury, Conn. All ingredients may be extruded into interlocking half shell capsules while in a pressurized vessel at a pressure of approximately 1.1 atmospheres (111.4 kPa). Such capsules may contain about 40 ml of a foaming aqueous cleaning solution as given below:

|  | % by weight |
| --- | --- |
| Water | 60.0 |
| Palmitic Acid | 4.0 |
| Stearic acid | 4.0 |
| Triethanolamine | 5.0 |
| Isopentane | 4.5 |
| Isobutane | 1.0 |
| n-butane | 0.5 |
| Sodium Lauryl Sulfate | ~20.0 |
| Glycerin | 2.5 |
| Acetic Acid (vehicle for fluorosurfactant) | 0.005 |
| Fluorosurfactant (Zonyl FSK) | 0.005 |

While the invention has been described in conjunction with several specific embodiments, it is to be understood that many alternatives, modifications, and variations will be apparent to those skilled in the art in light of the foregoing description. Accordingly, this invention is intended to embrace all such alternatives, modifications, and variations that fall within the spirit and the scope of the appended claims.

We claim:

1. A personal cleansing article comprising:
   a capsule, having a water-soluble shell with an exterior surface, an interior surface, and a barrier layer on the interior surface of the shell, and
   a liquid cleansing composition contained within the capsule, where the liquid cleaning composition comprises an aqueous based composition having one or more surfactants,
   where the capsule has a trigger such that upon occurrence of a specific event, the capsule releases the liquid cleansing composition contained therein,
   where the liquid cleansing composition further comprises a foaming agent, and
   where the foaming agent is a propellant gas.

2. The article of claim 1, where a capsule further comprises an interlocking outer shell assembly having a first outer shell and a second outer shell adapted to interlock and contain the liquid cleansing composition therein.

3. The article of claim 1, where the capsule is a seamless shell.

4. The article of claim 1, where the trigger is a water-soluble shell that releases the liquid cleansing composition upon exposing the capsule to water.

5. The article of claim 1, where the trigger is a pressure-sensitive shell that releases the liquid cleansing composition upon exposing the capsule to an external pressure source.

6. The article of claim 1, where the trigger is a shell that is both water-soluble and pressure sensitive such that the liquid cleansing composition is released from the capsule upon exposing the capsule to water, an external pressure source, or both.

7. The article of claim 1, where the barrier layer comprises a layer of microcrystalline wax.

8. The article of claim 1, where the liquid cleansing composition further comprises a co-surfactant.

9. The article of claim 1, where the liquid cleansing composition further comprises a therapeutic benefit agent.

10. The article of claim 1, where the at least one of the surfactants is a fluorinated surfactant.

11. The article of claim 1, where the capsule further comprises a plurality of micro-capsules contained within the capsule and where the liquid cleansing composition is encapsulated within such microcapsules.

12. A method for personal cleansing comprising the steps:
   providing the personal cleansing article according to claim 1;
   triggering the capsule to release the liquid cleansing composition from the capsule; and
   cleansing with the liquid cleansing composition.

13. The method of claim 12, where the step of triggering the capsule comprises exposing the capsule to water.

14. The method of claim 12, where the step of triggering the capsule comprises exposing the capsule to an external pressure source.

15. The method of claim 12, where the step of triggering the capsule comprises exposing the capsule to water, external pressure source, or both.

16. The method of claim 12, further comprising the step of foaming the liquid cleansing composition after triggering the release of the composition and prior to cleansing with the composition.

17. The method of claim 12, further comprising the step of providing more than one single-dose capsules containing liquid cleansing composition and triggering all of the capsules to release the liquid cleaning composition prior to cleansing with the composition.

18. A method for manufacturing a personal cleaning article according to claim 1 comprising the steps:
   a) providing a capsule shell material;
   b) forming a capsule from the capsule shell material;
   c) providing a pressurized enclosure;
   d) conveying the capsule into the pressurized enclosure;
   e) filling the capsule with a mixture of the liquid cleansing composition and the propellant gas;
   f) closing and sealing the capsule; and
   g) conveying the finished capsule from the pressurized enclosure.

* * * * *